(12) United States Patent
Bowling et al.

(10) Patent No.: US 9,937,014 B2
(45) Date of Patent: Apr. 10, 2018

(54) SYSTEM AND METHOD OF CONTROLLING A SURGICAL TOOL DURING AUTONOMOUS MOVEMENT OF THE SURGICAL TOOL

(71) Applicant: MAKO Surgical Corp., Ft. Lauderdale, FL (US)

(72) Inventors: David Gene Bowling, Los Ranchos de Albuquerque, NM (US); Patrick Roessler, Merzhausen (DE)

(73) Assignee: MAKO SURGICAL CORP., Fort Lauderdale, FL (US)

( * ) Notice: Subject to any disclaimer, the term of this patent is extended or adjusted under 35 U.S.C. 154(b) by 16 days.

(21) Appl. No.: 15/092,765

(22) Filed: Apr. 7, 2016

(65) Prior Publication Data

US 2016/0296296 A1    Oct. 13, 2016

Related U.S. Application Data

(60) Provisional application No. 62/145,584, filed on Apr. 10, 2015.

(51) Int. Cl.
*A61B 34/32* (2016.01)
*B25J 9/16* (2006.01)
(Continued)

(52) U.S. Cl.
CPC ............ *A61B 34/32* (2016.02); *A61B 34/30* (2016.02); *A61B 34/70* (2016.02); *A61B 34/76* (2016.02);
(Continued)

(58) Field of Classification Search
CPC ......... A61B 34/32; A61B 34/30; A61B 34/70; A61B 34/76; A61B 2034/107;
(Continued)

(56) References Cited

U.S. PATENT DOCUMENTS 9,119,655 B2    9/2015    Bowling et al.
9,274,014 B2    3/2016    Janik et al.
(Continued)

FOREIGN PATENT DOCUMENTS

EP          2666428 A1    11/2013
WO    WO 2007141784 A2    12/2007
WO    WO 2009092164 A1     7/2009

OTHER PUBLICATIONS

International Search Report and Written Opinion for PCT/US2016/026452 dated Jun. 16, 2016, 16 pages.

*Primary Examiner* — Bao Long T Nguyen
(74) *Attorney, Agent, or Firm* — Howard & Howard Attorneys PLLC

(57) ABSTRACT

A system and a method of controlling a surgical tool of a robotic system during autonomous movement of the surgical tool are provided. A path of movement for the surgical tool is determined. At least one acceptable orientation of the surgical tool with respect to the path is generated. The surgical tool autonomously moves along the path in the at least one acceptable orientation. Forces applied to the surgical tool are sensed. An altered orientation is identified based on the sensed forces. The surgical tool autonomously moves along the path in response to comparing the altered orientation to the at least one acceptable orientation.

26 Claims, 4 Drawing Sheets

(51) Int. Cl.
*A61B 34/30* (2016.01)
*A61B 34/00* (2016.01)
*A61B 90/00* (2016.01)
*A61B 34/10* (2016.01)
*A61B 34/20* (2016.01)

(52) U.S. Cl.
CPC ....... *B25J 9/1664* (2013.01); *A61B 2034/107* (2016.02); *A61B 2034/2055* (2016.02); *A61B 2034/2072* (2016.02); *A61B 2090/064* (2016.02); *A61B 2090/065* (2016.02); *G05B 2219/39325* (2013.01); *G05B 2219/45117* (2013.01)

(58) Field of Classification Search
CPC .... A61B 2034/2055; A61B 2034/2072; A61B 2090/064; A61B 2090/065; A61B 34/75; A61B 34/77; A61B 2090/0418; A61B 2090/066; B25J 9/1664; B25J 9/1633; B25J 9/1674; B25J 13/082; B25J 13/084–13/085; G05B 2219/39325; G05B 2219/45117; G05B 19/19; G05B 19/402; G05B 19/4061; G05B 2219/39088
USPC ........ 700/253, 250, 258; 318/568.16, 568.17
See application file for complete search history.

(56) References Cited

U.S. PATENT DOCUMENTS

| | | | |
|---|---|---|---|
| 9,566,122 B2* | 2/2017 | Bowling | A61B 34/32 |
| 2011/0306985 A1 | 12/2011 | Inoue et al. | |
| 2012/0029529 A1* | 2/2012 | Jun | A61B 34/30 606/130 |
| 2013/0041219 A1* | 2/2013 | Hasegawa | B25J 13/02 600/109 |
| 2014/0039681 A1* | 2/2014 | Bowling | A61B 34/32 700/261 |
| 2014/0052154 A1* | 2/2014 | Griffiths | B25J 9/1633 606/130 |
| 2014/0195052 A1* | 7/2014 | Tsusaka | B25J 3/04 700/257 |
| 2015/0100066 A1* | 4/2015 | Kostrzewski | A61B 34/30 606/130 |
| 2015/0196365 A1* | 7/2015 | Kostrzewski | A61B 17/3417 606/130 |
| 2016/0157964 A1* | 6/2016 | Suttin | A61C 8/0089 433/27 |

* cited by examiner

SYSTEM AND METHOD OF CONTROLLING A SURGICAL TOOL DURING AUTONOMOUS MOVEMENT OF THE SURGICAL TOOL

CROSS-REFERENCE TO RELATED APPLICATION

This application claims priority to and the benefit of U.S. provisional patent application No. 62/145,584, filed Apr. 10, 2015, the disclosure of which is hereby incorporated by reference in its entirety.

TECHNICAL FIELD

The present invention relates generally to a system and method of controlling a surgical tool during autonomous movement of the surgical tool.

BACKGROUND

Recently, medical practitioners have found benefit in using robotic systems to perform surgical procedures. Such a robotic system typically includes a moveable arm. The arm has a free, distal end that can be positioned with a high degree of accuracy. A surgical tool is attachable to the distal end of the arm. The surgical tool includes an energy applicator that is applied to a surgical site for treating the surgical site.

In some robotic systems, a medical practitioner manually manipulates the surgical tool to cause movement of the energy applicator with respect to the surgical site. This manual manipulation includes freely re-orienting the surgical tool at the surgical site. The medical practitioner may wish to manually re-orient the surgical tool to avoid obstacles such as retractors or other tissues at the surgical site. In other robotic systems, however, the surgical tool moves autonomously and the medical practitioner is unable to re-orient the surgical tool at the surgical site.

SUMMARY

The present disclosure provides a robotic system comprising a surgical tool being configured to move along a path. A manipulator supports the surgical tool and is configured to move the surgical tool along the path. A path generator determines the path. An orientation generator determines at least one acceptable orientation with respect to the path. A manipulator controller is in communication with the path generator and the orientation generator. The manipulator controller instructs the manipulator to autonomously move the surgical tool along the path in the at least one acceptable orientation. A sensor senses forces applied to the surgical tool. The manipulator controller is configured to identify an altered orientation based on the sensed forces and to instruct movement of the surgical tool along the path in response to comparing the altered orientation to the at least one acceptable orientation.

The present disclosure also provides a method of controlling a surgical tool of a robotic system during autonomous movement of the surgical tool. A path of movement for the surgical tool is determined. At least one acceptable orientation of the surgical tool with respect to the path is generated. The surgical tool autonomously moves along the path in the at least one acceptable orientation. Forces applied to the surgical tool are sensed. An altered orientation is identified based on the sensed forces. The surgical tool autonomously moves along the path in response to comparing the altered orientation to the at least one acceptable orientation.

In one embodiment, the system and method provide the advantage of controlling the surgical tool so that the orientation of the surgical tool is maintained in the at least one acceptable orientation. By doing so, the system and method avoid undesirable orientations of the surgical tool that could result in cutting inefficiency, contact with another object at the surgical site, or the like.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Figure 1:
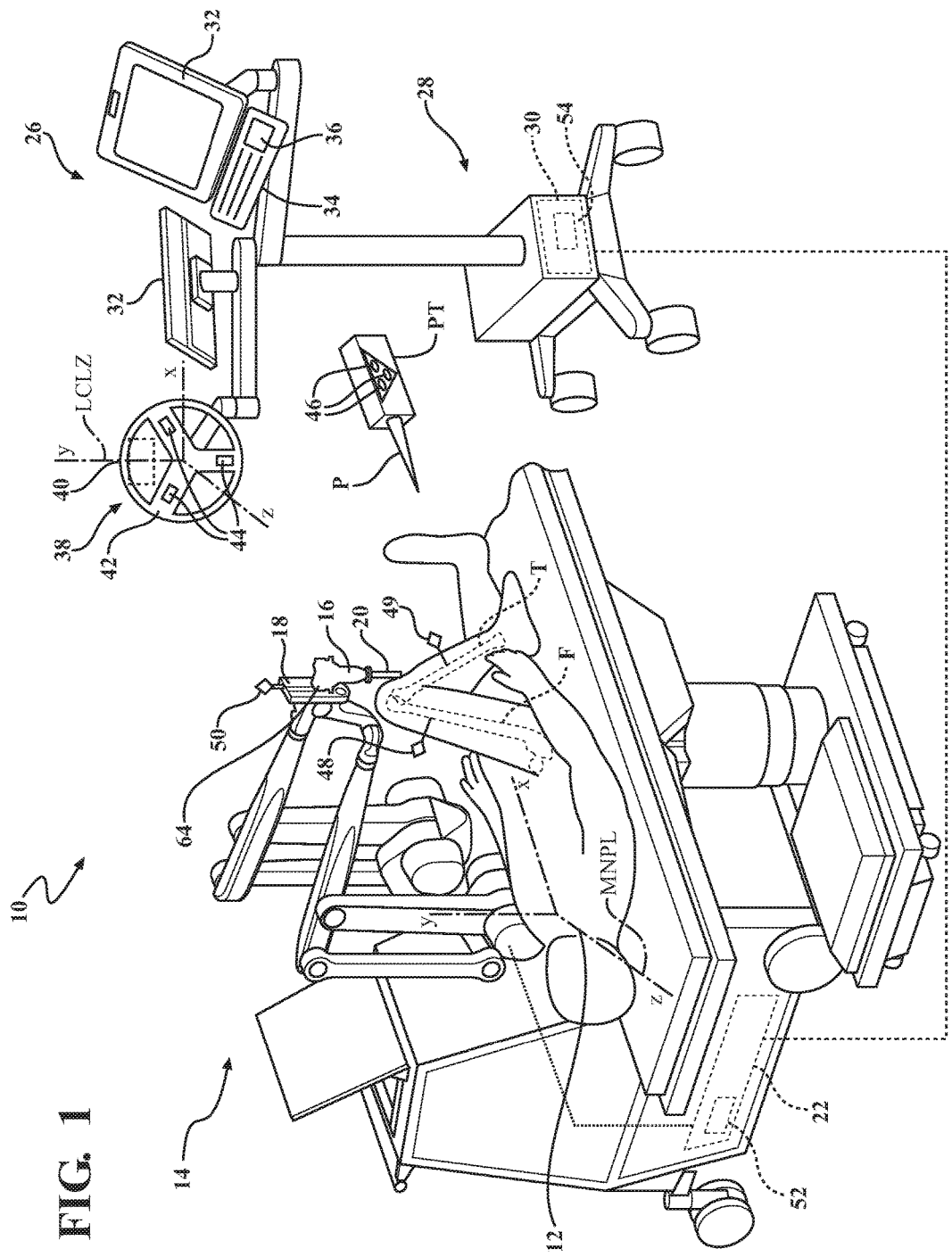
FIG. 1 is a perspective view of a robotic system.

Referring to FIG. 1, a robotic system 10 for performing a surgical procedure on a patient 12 is shown. The surgical procedure described herein is a tissue removal procedure. Tissue may be bone or any other tissue of the patient. However, it is to be appreciated that the systems and methods disclosed herein may be used to perform other procedures, surgical or non-surgical, or may be used in industrial applications or other applications where robotic systems are utilized.

The robotic system 10 includes a manipulator 14 and a surgical tool 16. The surgical tool 16 forms part of an end effector 18 attached to the manipulator 14. The surgical tool 16 is designed to be grasped by a hand of the operator. One exemplary arrangement is shown in U.S. patent application Ser. No. 13/958,070, entitled, "Surgical Manipulator Capable of Controlling a Surgical Instrument in Multiple Modes," the disclosure of which is hereby incorporated by reference. The manipulator 14 and the surgical tool 16 may be arranged in alternative configurations. The surgical tool 16 includes an energy applicator 20 designed to contact the tissue of the patient 12 at a surgical site. The energy applicator 20 may be a drill, a saw blade, a bur, an ultrasonic tip, or the like. The manipulator 14 also houses a manipulator computer 22, or other type of control unit.

The robotic system 10 is capable of operating in a semi-autonomous mode or a manual mode. In the semi-autonomous mode, the manipulator 14 directs autonomous movement of the surgical tool 16 and, in turn, the energy applicator 20 at the surgical site. In one embodiment, when the robotic system 10 is in the semi-autonomous mode, the manipulator 14 is capable of moving the surgical tool 16 free of operator assistance. Free of operator assistance may mean that an operator does not physically contact the surgical tool 16 to move the surgical tool 16. Instead, the operator may use some form of remote control to control starting and stopping of movement. For example, the operator may hold down a button of the remote control to start movement of the surgical tool 16 and release the button to stop movement of the surgical tool 16.

In the manual mode, the operator physically contacts the surgical tool 16 to cause movement of the surgical tool 16, as described in U.S. patent application Ser. No. 13/958,070, entitled, "Surgical Manipulator Capable of Controlling a Surgical Instrument in Multiple Modes," the disclosure of which is hereby incorporated by reference.

Figure 2:
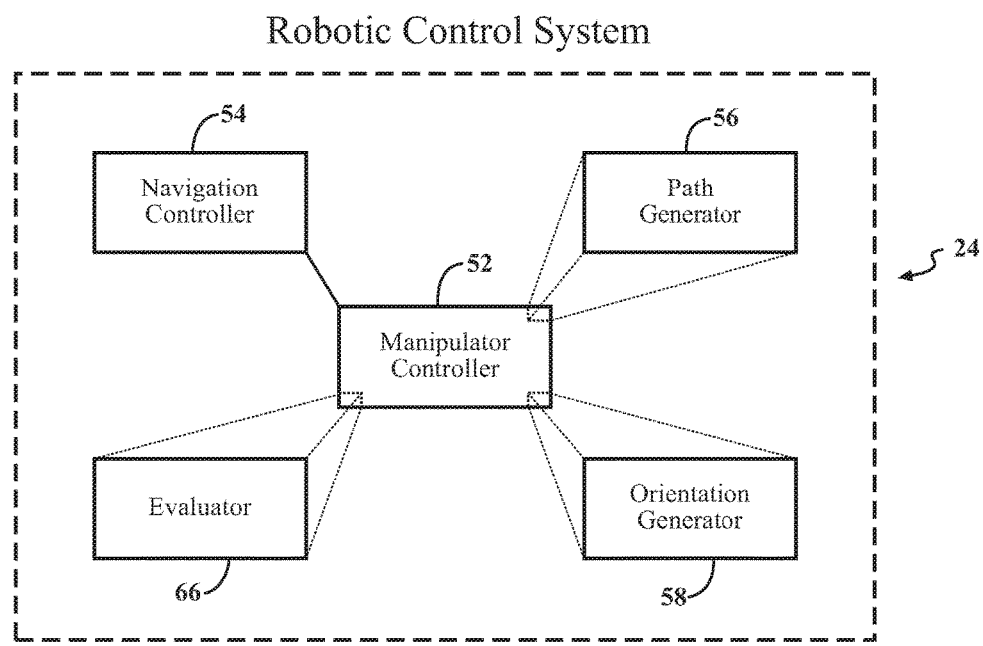
FIG. 2 is a schematic view of a robotic control system.

Referring to FIG. 2, the robotic system 10 includes a robotic control system 24. The robotic control system 24 includes software and/or hardware for directing the motion of the manipulator 14. The robotic control system directs the motion of the manipulator 14 and controls an orientation of the surgical tool 16 during the surgical procedure. The orientation of the surgical tool 16 is defined within a coordinate system. In one embodiment, the coordinate system is a manipulator coordinate system MNPL (see FIG. 1). The manipulator coordinate system MNPL has an origin, and the origin is located at a point on the manipulator 14. One example of the manipulator coordinate system MNPL is shown in U.S. patent application Ser. No. 13/958,070, entitled, "Surgical Manipulator Capable of Controlling a Surgical Instrument in Multiple Modes," the disclosure of which is hereby incorporated by reference.

The robotic system 10 includes a guidance station 26. The guidance station 26 is set up to track movement of various objects. Such objects include, for example, the surgical tool 16, a femur F, and a tibia T. The guidance station 26 tracks these objects to gather position information of each object in a localizer coordinate system LCLZ. Coordinates in the localizer coordinate system LCLZ may be transformed to the manipulator coordinate system MNPL using conventional transformation techniques. The guidance station 26 is also capable of displaying a virtual representation of their relative positions and orientations to a surgeon.

The guidance station 26 includes a computer cart assembly 28 that houses a navigation computer 30, and/or other types of control units. A navigation interface is in operative communication with the navigation computer 30. The navigation interface includes one or more displays 32. First and second input devices 34, 36 such as a keyboard and mouse may be used to input information into the navigation computer 30 or otherwise select/control certain aspects of the navigation computer 30. Other input devices are contemplated including a touch screen (not shown) or voice-activation.

The guidance station 26 also includes a localizer 38 that communicates with the navigation computer 30. In one embodiment, the localizer 38 is an optical localizer and includes a camera unit 40. The camera unit 40 has an outer casing 42 that houses one or more optical position sensors 44. The robotic system 10 includes one or more trackers. The trackers may include a pointer tracker PT, a surgical tool tracker 50, a first patient tracker 48, and a second patient tracker 49. The trackers include active markers 46. The active markers 46 may be light emitting diodes or LEDs. In other embodiments, the trackers 48, 49, 50 may have passive markers, such as reflectors, which reflect light emitted from the camera unit 40. Additional trackers may be incorporated into the robotic system 10 to track additional components that may be part of the robotic system 10. For example, trackers may be attached to retractors (not shown) used to retract tissue around a knee joint during placement of implant components.

In the illustrated embodiment of FIG. 1, the first patient tracker 48 is firmly affixed to the femur F of the patient 12 and the second patient tracker 49 is firmly affixed to the tibia T of the patient 12. The patient trackers 48, 49 are firmly affixed to sections of bone. In addition, the surgical tool tracker 50 is firmly attached to the surgical tool 16. It should be appreciated that the trackers 48, 49, 50 may be fixed to their respective components in any suitable manner.

The trackers 48, 49, 50 communicate with the camera unit 40 to provide position data of the trackers 48, 49, 50 to the camera unit 40. The camera unit 40 then provides the position data of the trackers 48, 49, 50 to the navigation computer 30. In one embodiment, the navigation computer 30 then determines and communicates position data of the femur F and tibia T and position data of the surgical tool 16 to the manipulator computer 22. Position data for the femur F, tibia T, and surgical instrument 16 may be determined by the tracker position data using conventional registration/navigation techniques. The position data includes position information corresponding to the position and/or orientation of the femur F, tibia T, surgical instrument 16 and any other objects being tracked. The position data described herein may be position data, orientation data, or a combination of position data and orientation data.

The manipulator computer 22 may transform the position data from the localizer coordinate system LCLZ into the manipulator coordinate system MNPL by determining a transformation matrix using the navigation-based data for the surgical tool 16 and encoder-based position data for the surgical tool 16. Encoders (not shown) located at joints of the manipulator 14 are used to determine the encoder-based position data. The manipulator computer 22 uses the encoders to calculate an encoder-based position and orientation of the surgical tool 16 in the manipulator coordinate system MNPL. Since the position and orientation of the surgical tool 16 is also known in the localizer coordinate system LCLZ, the transformation matrix can be generated.

The robotic control system 24 further includes software modules. The software modules may be part of a computer program or programs that operate on the manipulator computer 22, navigation computer 30, or a combination thereof, to process data to assist with control of the robotic system 10. The software modules include sets of instructions stored in memory on the manipulator computer 22, navigation computer 30, or a combination thereof, to be executed by one or more processors of the computers 22, 30. Additionally, software modules for prompting and/or communicating with the medical practitioner may form part of the program or programs and may include instructions stored in memory on the manipulator computer 22, navigation computer 30, or a combination thereof. The surgeon interacts with the first and second input devices 34, 36 and the one or more displays 32 to communicate with the software modules.

In one embodiment, the manipulator computer 22 includes a manipulator controller 52 for processing data for directing the motion of the manipulator 14. The manipulator controller 52 may receive and process data from a single source or multiple sources. In one embodiment, the navigation computer 30 includes a navigation controller 54 for communicating the position data relating to the femur F, tibia T, and instrument 16 to the manipulator controller 52. The manipulator controller 52 receives and processes the position data provided by the navigation controller 54 to direct movement of the manipulator 14.

The manipulator controller 52 may also communicate positions of the patient 12 and surgical instrument 16 to the surgeon by displaying an image of the femur F and/or tibia T and the surgical tool 16 on the one or more displays 32. The manipulator computer 22 may also display instructions or request information on the one or more displays 32 such that the surgeon may interact with the manipulator computer 22 for directing the manipulator 14.

Referring to FIG. 2, the robotic control system 24 further includes a path generator 56 and an orientation generator 58. In one embodiment, the path generator 56 and the orientation generator 58 are both software modules. The software modules may operate on the manipulator controller 52 or any other suitable component in the robotic system 24.

Figure 3:
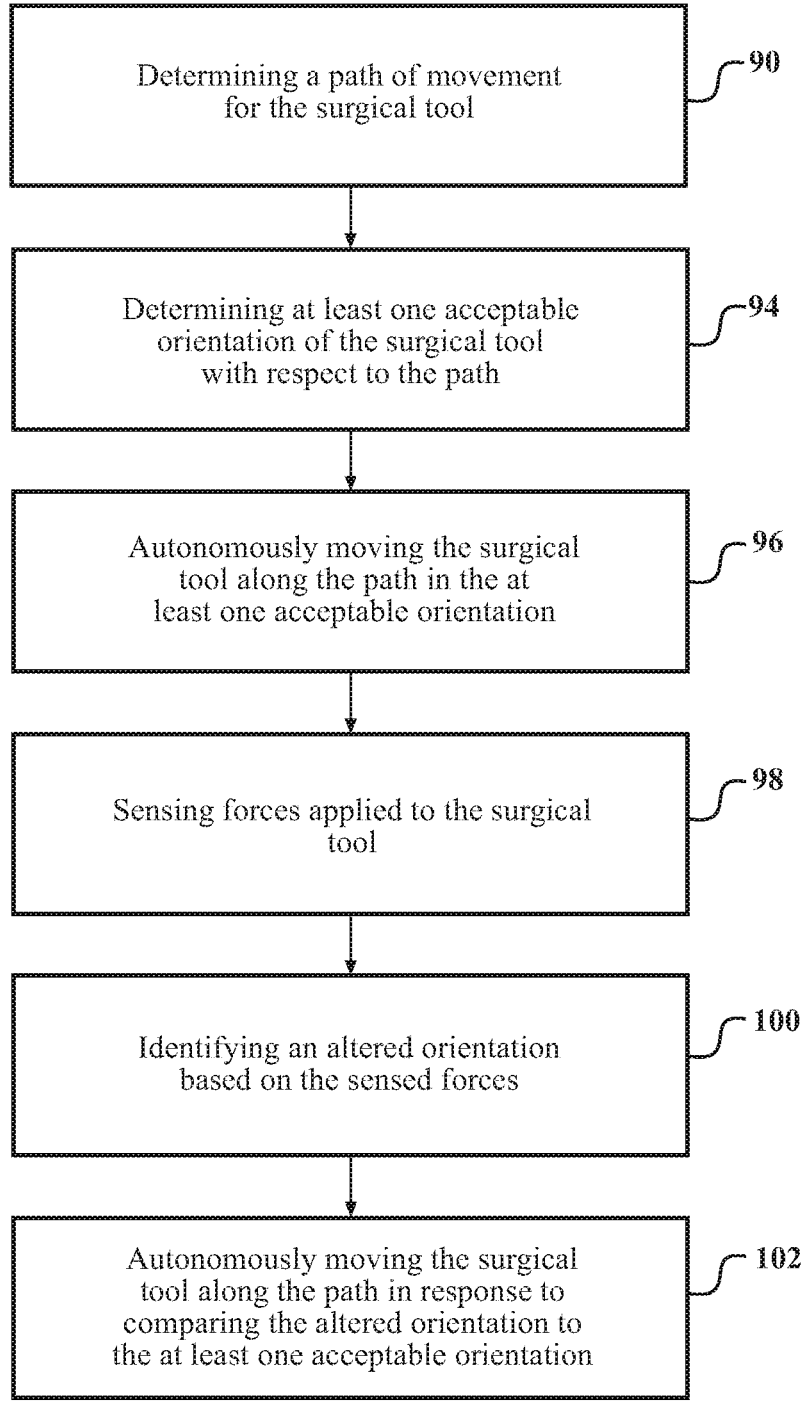
FIG. 3 provides steps performed in one embodiment.

As shown in FIG. 3, the path generator 56 determines a path of movement for the surgical tool 16 in step 90. One example of the path is shown at 60 in FIG. 4. The path generator 56 determines the path 60 for the surgical tool 18 to move along in the manipulator coordinate system MNPL. In addition, the path generator 56 generates path data related to the path 60 and communicates the path data to the manipulator controller 52. The path generator 56 may provide pre-operative, and/or intra-operative path data to the manipulator controller 52 such that the path 60 may be updated at any time during the surgical procedure. This feature is described in U.S. patent application Ser. No. 13/958,070, entitled, "Surgical Manipulator Capable of Controlling a Surgical Instrument in Multiple Modes," the disclosure of which is hereby incorporated by reference.

In one embodiment, the path 60 is defined in, or through, bone. For example, the path 60 may be defined to allow the surgical tool 18 to cut and remove a volume of bone such that the bone may receive an implant (not shown). The path 60 may correspond to a particular volume of bone to be cut to receive a specific geometry (e.g., size and shape) of implant.

The path generator 56 generates path data using data provided by the robotic control system 24 and relating to the patient 12, the surgical tool 16, the implant, and/or any other object located at the surgical site. The data input into the path generator 56 may include femur and/or tibia pose data, surgical tool 16 pose data, other object pose data, imaging data (e.g., CT/MRI data), data defining the shape of a boundary across which the surgical tool 16 is not to extend and/or data defining the volume of tissue to be removed by the surgical tool 16, implant data, and data relating to the surgeon's setting of the location of the boundary. The path generator 56 processes the data to generate the cutting path.

In some implementations, path generator 56 also receives as an input a solid body model of the material to be removed. In another implementation, the path generator 56 generates the solid body model based on the inputs of the image of the tissue, the data defining the shape of the boundary, and the surgeon settings. For an orthopedic surgical procedure, the boundary is typically the shape of the implant and the surgeon setting is often the position of the implant. Based on these data, the path generator 56 defines the path 60. Each tool path segment may be defined as a vector or a curve that extends between points present in a bone coordinate system. The path segments are defined in three dimensions. This is because the surgical tool 16 is not just applied in a single plane to the tissue. The surgical tool 16 also moves up or down in order to contact tissue in the plane above or below the plane in which it is presently located.

The path generator 56 then generates path data relating to the cutting path and communicates the path data to the manipulator controller 52. The robotic control system 24 may provide the data to the path generator 36 at any time during the surgical procedure to update the path.

Figure 4:
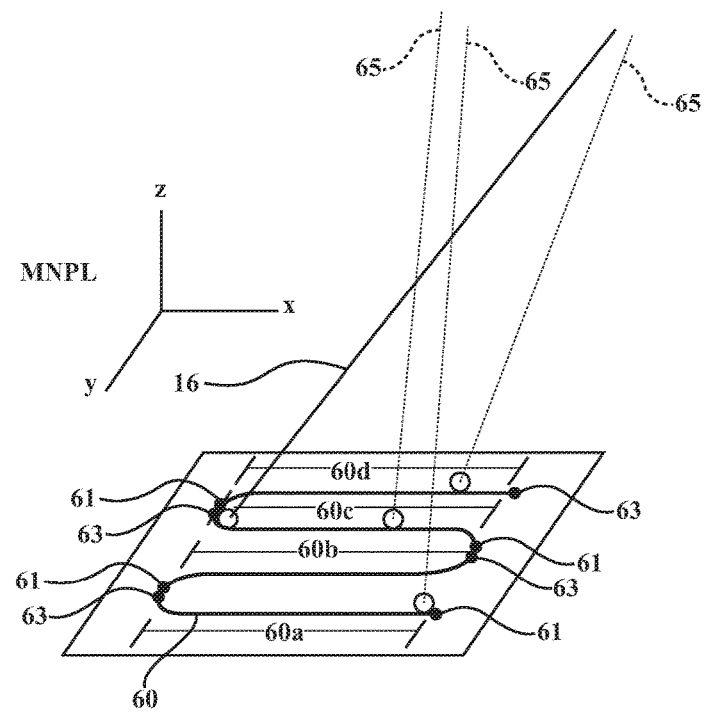
FIG. 4 is an illustration of a surgical instrument moving in at least one acceptable orientation along a path.

In another embodiment, the path 60 is divided into one or more segments. For example, as shown in FIG. 4, the path 60 is divided into four segments 60a-60d, with each segment 60a-60d having a first endpoint 61 and a second endpoint 63. For each segment 60a-60d of the path 60, the path generator 56 may process the data provided by the robotic control system 24 to generate path segment data. Although only four segments 60a-60d are described and illustrated in FIG. 4, those skilled in the art appreciate that the path 60 may be divided into any suitable number of segments. For instance, referring to FIGS. 5A and 5B, the path 60 shown could comprise seven segments with each straight portion being separate segments and each curved portion being separate segments. The segments may each be of similar length, or may be of varying lengths.

In one embodiment and as illustrated in FIG. 4, the path generator 56 generates path data relating to the path 60 on bone or other tissue of the patient 12 to be treated. The path generator 56 determines the path 60 for the surgical tool 16 and in turn, the energy applicator 20, to move along the bone such that the energy applicator 20 removes bone from the patient 12 as the surgical tool 16 is moved along the path 60. The bone removed from the patient 12 may be a volume of bone.

Figure 5A:
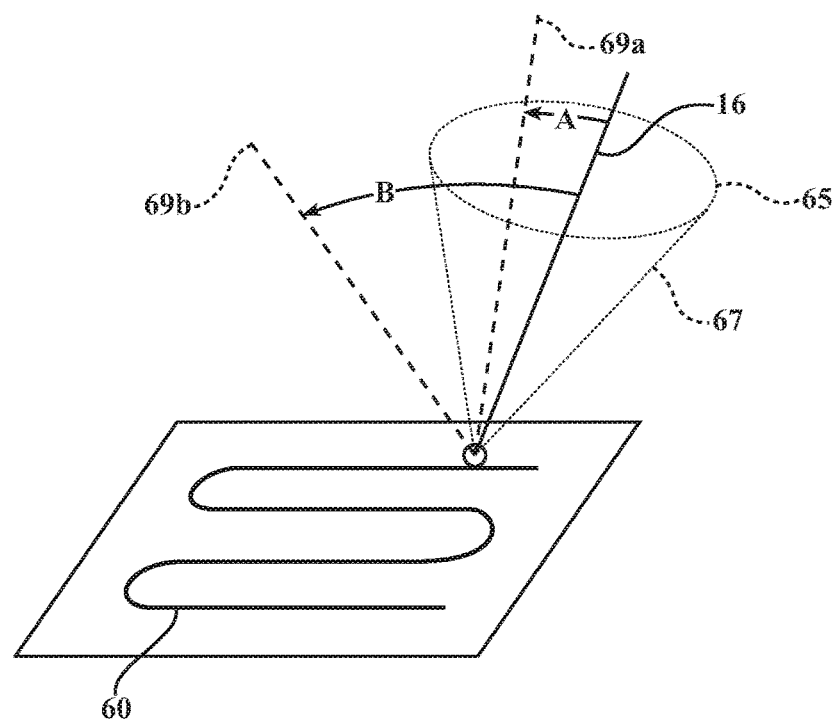
FIG. 5A and FIG. 5B are illustrations comparing altered orientations of the surgical tool to the at least one acceptable orientation of the surgical tool.
Figure 5B:
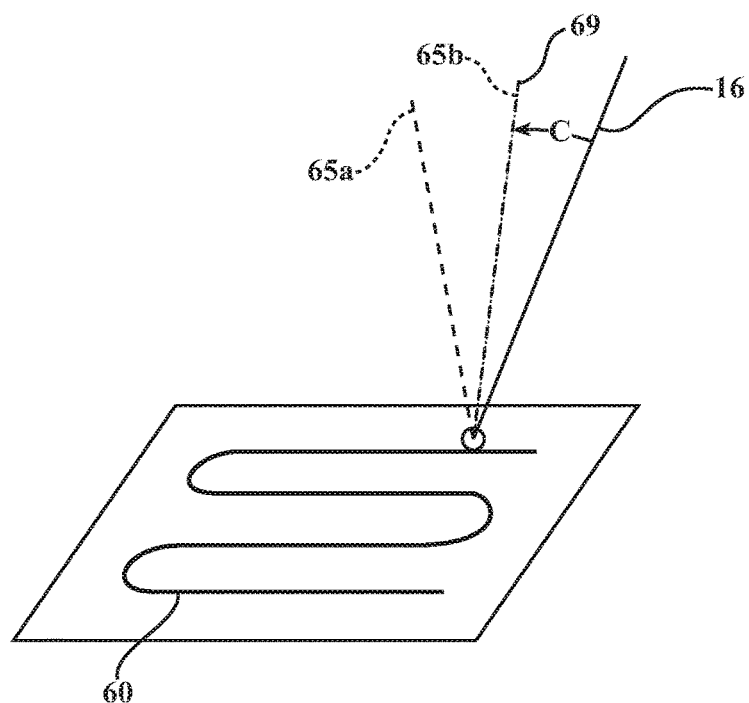

Referring to FIG. 2 and FIG. 3, the orientation generator 58 determines at least one acceptable orientation 65 of the surgical tool 16 with respect to the path 60 in step 94. In FIGS. 4, 5A and 5B, an actual orientation of the surgical tool 16 is identified by a solid line and the at least one acceptable orientation 65 is shown as a dotted line.

In one embodiment, the orientation generator 58 communicates with the manipulator controller 52 and determines the at least one acceptable orientation 65 of the surgical tool 16 with respect to the path 60. The orientation generator 58 generates orientation data relating to the at least one acceptable orientation 65. For any given moment, the at least one acceptable orientation 65 may be a single acceptable orientation 65 or a plurality of acceptable orientations 65.

The orientation generator 58 may determine the at least one acceptable orientation 65 with respect to the path 60 by assessing whether any obstacles exist along the path 60. If so, the orientation generator 58 determines acceptable orientations 65 to allow the surgical tool 16 to avoid such obstacles along the path 60. For instance, if the surgical procedure is a bone milling procedure, there may be certain orientations by which the surgical tool 16 avoids cutting objects at the surgical site. The obstacles may be any obstacle at the surgical site, such as retractors or tissues. In determining the at least one acceptable orientation 65, the orientation generator 58 may retrieve information about such obstacles from the navigation system computer 30, tool path generator 56, and the like.

Additionally or alternatively, the orientation generator 58 may determine the at least one acceptable orientation 65 with respect to the path 60 to optimize cutting efficiency of the surgical tool 16 along the path 60 The orientation generator 58 determines acceptable orientations 65 to allow the surgical tool 16 to efficiently cut along the path 60. For instance, if the surgical procedure is a bone milling procedure, the surgical tool 16 may have a preferred orientation or preferred range of orientations to avoid cutting inefficiencies. The surgical tool 16 may more efficiently cut at certain orientations as compared with others. Parameters regarding cutting efficiency of the surgical tool 16 in various scenarios may be stored in memory and accessed by the orientation generator 58. Cutting efficiency of the surgical tool 16 may be determined according to any suitable method.

The at least one acceptable orientation 65 of the surgical tool 16 may be a range 67 of acceptable orientations 65. As shown in FIG. 5A, the range 67 of acceptable orientations 65 may be defined by a volume in coordinate system MNPL. In FIG. 5A, the range of acceptable orientations 65 is defined by a cone where a tip of the energy applicator 20 is the vertex of the cone. The range 67 of acceptable orientations 65 may be defined as any orientation along a perimeter of and/or within the volume. In other examples, the range of acceptable orientations 65 may be defined by a two-dimensional area or plane in the manipulator coordinate system MNPL. The range 67 of acceptable orientations 65 may be determined pre-operatively and/or updated intra-operatively.

As shown in FIG. 5B, the at least one acceptable orientation 65 may be one or more discrete acceptable orientations. There may be any suitable number of discrete acceptable orientations.

In one embodiment, the orientation generator 58 generates a preferred subset of the at least one acceptable orientation 65, i.e., at least one preferred orientation. For instance, a virtual aperture may be located above the tissue with the preferred subset of the at least one acceptable orientation 65 being orientations in which the surgical tool 16 is maintained within the virtual aperture. Thus, there may be other acceptable orientations 65 in which the surgical tool 16 falls outside of the virtual aperture, i.e., outside of the preferred orientations, but still within the at least one acceptable orientation 65. The preferred subset may be determined to optimize operational efficiency of the surgical tool 16.

As shown in FIG. 4, in some embodiments, the orientation generator 58 provides the at least one acceptable orientation 65 for each segment 60a-60d of the path 60. The at least one acceptable orientation 65 may be different for each segment 60a-60d of the path 60, similar for like segments 60a-60d, or the same along multiple segments 60a-60d. The orientation generator 58 may receive, as an input, femur and/or tibia pose data, other object pose data, imaging data (e.g., CT/MRI data), data defining the shape of the boundary across which the surgical tool 16 is not to extend and/or data defining the volume of tissue to be removed by the surgical tool 16, implant data, data relating to the surgeon's setting of the location of the boundary, data defining the virtual aperture at the surgical site, and data defining the path 60 along which the surgical tool 16 is to traverse.

In one exemplary implementation when cutting the femur F, the orientation generator 58 selects the orientation of the surgical tool 16 that results in the orientation of the surgical tool 16 being parallel to a longitudinal axis of the femur F. In this implementation, the orientation generator 58 receives data defining the path 60 and femur pose data including the orientation of the longitudinal axis. In this instance, the orientation generator 58 updates the at least one acceptable orientation 65 for each path segment 60a-60d intraoperatively to account for movement of the longitudinal axis. In other implementations, the orientation generator 58 may select the range 67 of acceptable orientations 65 for each segment 60a-60d of the path 60 so that the surgical tool 16 avoids obstacles at the surgical site.

The orientation generator 58 communicates the orientation data relating to the at least one acceptable orientation 65 of the surgical tool 16 to the manipulator controller 52. The manipulator controller 52 processes the orientation data and directs the manipulator 14 to orient the surgical tool 16 when the surgical tool 16 moves autonomously along the path, as disclosed in U.S. patent application Ser. No. 13/958,070, entitled, "Surgical Manipulator Capable of Controlling a Surgical Instrument in Multiple Modes," the disclosure of which is hereby incorporated by reference.

Referring to FIG. 3, the surgical tool 16 autonomously moves along the path 60 in the at least one acceptable orientation 65, in step 96. The manipulator controller 52 communicates with the path generator 56 and the orientation generator 58 to instruct the manipulator 14 to autonomously move the surgical tool 16 along the path 60 and in the at least one acceptable orientation 65. The manipulator 14, in the semi-autonomous, autonomously moves the surgical tool 16 along the path 60 without the operator handling the surgical tool 16 or free of operator assistance. The surgical tool 16 is placed in the at least one acceptable orientation 65 when the surgical tool 16 autonomously moves along the path 60. As shown in FIG. 4, the manipulator 14 places the surgical tool 16 in the at least one acceptable orientation 65 when the surgical tool 16 moves from the first endpoint 61 to the second endpoint 63 along each segment 60a-60d of the path 60.

In some embodiments, the manipulator controller 52 includes an orientation regulator (not shown) that maintains the actual orientation of the surgical tool 16 within the at least one preferred orientation during normal operation in the semi-autonomous mode. This is described in U.S. patent application Ser. No. 13/958,070, entitled, "Surgical Manipulator Capable of Controlling a Surgical Instrument in Multiple Modes," the disclosure of which is hereby incorporated by reference. In one embodiment, the orientation regulator works to maintain the orientation of the surgical tool 16 within the preferred subset of the at least one acceptable orientation 65 as the surgical tool 16 moves along the path 60. For instance, the orientation regulator may maintain the surgical tool 16 within the virtual aperture located above the tissue.

During a surgical procedure, there may be an attempt to alter the orientation of the surgical tool 16 as the surgical tool 16 moves autonomously along the path 60. Forces are applied to the surgical tool 16 when attempting to place the surgical tool 16 in the altered orientation 69. FIGS. 5A and 5B illustrate the altered orientation 69 of the surgical tool 16 in relation to the actual orientation of the surgical tool 16. An arrow between the actual orientation and the altered orientation 69 represents anticipated movement of the actual orientation of the surgical tool 16 based on the applied forces.

Alteration of the orientation of the surgical tool 16 typically results from manual interruption during the semi-autonomous mode. For instance, it may be necessary for the operator to alter the orientation of the surgical tool 16 if the surgical tool 16 contacts, or is about to contact, an object such as tissue that is not to be treated. If the surgical tool 16 contacts, or is about to contact, such an object, the operator may need to alter the orientation of the surgical tool 16 to an altered orientation 69. Thus, the altered orientation 69 occurs through manual intervention. The altered orientation 69 may be an orientation desired by the operator. Of course, those skilled in the art realize that the orientation may be altered even when the operator does not specifically desire so. For example, forces may be inadvertently applied to the surgical tool 16 by mistake causing an attempt to alter the orientation of the surgical tool 16 during autonomous movement.

Referring to FIG. 3, a sensor 64 senses forces applied to the surgical tool 16 in step 98. One such sensor is shown in U.S. patent application Ser. No. 14/199,299 entitled, "Sensor Assembly and Method for Measuring Forces and Torques," the disclosure of which is hereby incorporated by reference. Referring back to FIG. 1, the sensor 64 is coupled to the surgical tool 16. The sensor 64 can be integrated with the surgical tool 16, or the manipulator 14 in alternative embodiments. Forces applied to the surgical tool may be any suitable applied forces, including, but not limited to, rotational forces, axial forces, and the like. Additionally or alternatively, forces applied to the surgical tool 16 may be deduced from measurements of the sensor 64, such as stress measurements. Torques applied to the surgical tool 16 may also be deduced from measurements by the sensor 64. The operator or any other external force may apply the forces and/or torques to the surgical tool 16. The sensor 64 generates sensor data relating to the forces applied to the surgical tool 16 in attempting to place the surgical tool 16 in the altered orientation 69.

In some embodiments, a button is located on the surgical tool 16 that is depressed when the operator wants to alter the orientation. Such a button is shown and described in U.S. patent application Ser. No. 13/958,070, entitled, "Surgical Manipulator Capable of Controlling a Surgical Instrument in Multiple Modes," the disclosure of which is hereby incorporated by reference. Depressing the button signals that the operator desires to place the surgical tool 16 into the altered orientation 69.

In some cases, if the button is not depressed, but a relatively large force (as compared with normal re-orienting forces) is placed on the surgical tool 16 when in the semi-autonomous mode (as sensed by the sensor 64) then the manipulator controller 52 may suspend advancement of the energy applicator 20 along the path. The large force may be a result of the operator attempting to re-orient the surgical tool 16 without first depressing the button or it may be a result of the surgical tool 16 abutting another object such as a retractor. Sensed forces on the surgical tool 16 may be monitored in relation to a predetermined threshold. If the forces exceed the predetermined threshold, the forces may be determined to be abnormal or large. The manipulator controller 52 may display a message to the operator on the display 32 requesting confirmation that the operator wants to alter the orientation. If the operator confirms, then the robotic control system 24 next determines whether the altered orientation 69 desired by the operator is acceptable.

At step 100 in FIG. 3, the altered orientation 69 is identified based on the sensed forces. The manipulator controller 52 receives and evaluates the sensor data from the sensor 64. The manipulator controller 52 determines the altered orientation 69 based on the sensor data. By doing so, the manipulator controller 52 predicts how and to where the orientation of the surgical tool 16 would move if the manipulator 14 were to react instantaneously to the forces applied to the surgical tool 16 in order to re-orient the surgical tool 16. The identified altered orientation 69 may be stored in memory and later accessed by the manipulator controller 69. The altered orientation 69 can be calculated in the manner described in U.S. patent application Ser. No. 13/958,070, entitled, "Surgical Manipulator Capable of Controlling a Surgical Instrument in Multiple Modes," the disclosure of which is hereby incorporated by reference.

The manipulator controller 52 is configured to evaluate the altered orientation 69. The manipulator controller 52 controls the manipulator 14 so that the manipulator 14 delays movement of the surgical tool 16 to the altered orientation 69 until the altered orientation 69 is evaluated.

Referring back to FIG. 3, the manipulator controller 52 is configured to compare the altered orientation 69 to the at least one acceptable orientation 54 at step 102. The manipulator controller 52 autonomously moves the surgical tool 16 along the path 60 in response to this comparison, at step 102.

An evaluator 66 is a software module that runs on the manipulator controller 52. In one embodiment, the evaluator 66 evaluates the altered orientation 69 to compare the altered orientation 69 to the at least one acceptable orientation 65. The evaluator 66 may reference a look-up table stored in the manipulator computer 22 that identifies the at least one acceptable orientation 65 of the surgical tool 16 for each path 60 or segment 60a-60d of the path. The evaluator 66 may rely on the look-up table to compare the altered orientation 69 with the at least one acceptable orientation 65 for the path or the particular segment of the path on which the surgical tool 16 is located. The evaluator 66 may rely on the look-up table by comparing the altered orientation 69 against look-up table orientations. The evaluator 66 provides evaluation data to the manipulator controller 52 relating to the evaluation made by the evaluator 66.

The altered orientation 69 may or may not correspond to the at least one acceptable orientation 65. In determining whether the altered orientation 69 corresponds to the at least one acceptable orientation 65, the manipulator controller 52 evaluates whether or not the altered orientation 69 falls within the at least one acceptable orientation 65. In other words, the manipulator controller 52 evaluates whether the altered orientation 69 aligns with one of the discrete acceptable orientations 65 or one of the acceptable orientations 65 in the range 67. Alignment between the altered orientation 69 and the acceptable orientation 65 may be assessed according to any suitable algorithm or method.

In some instances, alignment between the altered orientation 69 and the acceptable orientation 65 must be exact to determine that the altered orientation 69 corresponds to the at least one acceptable orientation 65. In other instances, alignment between the altered orientation 69 and the acceptable orientation 65 need not be exact to determine that the altered orientation 69 corresponds to the at least one acceptable orientation 65. In such instances, the altered orientation 69 and the at least one acceptable orientation 65 may be substantially aligned. For example, the manipulator controller 52 may determine that the altered orientation 69 corresponds to the at least one acceptable orientation 65 in instances where the alignment of the orientations 65, 69 is within a certain threshold.

In one instance, the manipulator controller 52 is configured to maintain the surgical tool 16 in the at least one acceptable orientation 65 in response to comparing the altered orientation 69 to the at least one acceptable orientation 65. For example, the manipulator controller 52 is configured to maintain the surgical tool 16 in the at least one acceptable orientation 65 in response to determining that the altered orientation 69 does not correspond to the at least one acceptable orientation 65. The manipulator controller 52 responds to the evaluation of the altered orientation 69 and maintains the surgical tool 16 in the at least one acceptable orientation 65 as the surgical tool 16 moves with respect to the path 60.

An example of this scenario is shown in FIG. 5A, wherein the acceptable orientations 65 with respect to the path 60 are illustrated by the range 67 defined by the conical volume. The actual orientation of the surgical tool 16 begins within the range 67 and is one of the acceptable orientations 65. Forces (B) are applied to the surgical tool 16 and the manipulator controller 52 identifies the altered orientation 69b based on the sensed forces. The altered orientation 69b is identified beyond the range 67 of the acceptable orientations 65. Thus, the altered orientation 69b does not correspond to the at least one acceptable orientation 65. In other words, the altered orientation 69b is not acceptable. Thus, the manipulator controller 52 maintains the surgical tool 16 in the at least one acceptable orientation 65, and more specifically, in the actual orientation.

If the evaluator 66 determines the altered orientation 69 does not fall within the at least one acceptable orientation 65, the evaluation data provided to the manipulator controller 52 instructs the manipulator 14 to prevent the movement of the surgical tool 16 into the altered orientation 69. The manipulator controller 52 processes the evaluation data provided by the evaluator 66 and directs the manipulator 14 to maintain the surgical tool 16 in the at least one acceptable orientation 65 as the surgical tool 16 moves with respect to the path. The manipulator controller 52 may prevent the movement of the surgical tool 16 into the altered orientation 69 by preventing movement of the surgical tool 16 altogether. Alternatively, the manipulator controller 52 may allow movement of the surgical tool 16 into the closest acceptable orientation 65 for a predetermined period, for a predetermined distance of movement, or until the surgical tool 16 reaches the next segment in the path 60.

In another instance, the manipulator controller 52 is configured to instruct movement of the surgical tool 16 to the altered orientation 69 in response to comparing the altered orientation 69 to the at least one acceptable orientation 65. More specifically, the manipulator controller 52 is configured to instruct movement of the surgical tool 16 to the altered orientation 69 in response to determining that altered orientation 69 corresponds to the at least one acceptable orientation 65. If there is the range 67 of acceptable orientations 65 and the altered orientation 69 falls within the range 67, then the manipulator controller 52 instructs the manipulator 14 to move the surgical tool 16 to the altered orientation 69.

One example of this scenario is shown in FIG. 5A, wherein the actual orientation of the surgical tool 16 begins within the range 67 and is one of the acceptable orientations 65. Forces (A) are applied to the surgical tool 16 and the manipulator controller 52 identifies the altered orientation 69*a* based on the sensed forces. The altered orientation 69*a* is identified within the range 67 of the acceptable orientations 65. Thus, the altered orientation 69*a* corresponds to the at least one acceptable orientation 65. In other words, the altered orientation 69*a* is acceptable. The manipulator controller 52 allows the surgical tool 16 to move from its actual position to the altered orientation 69*a* within the range 67. Another example is illustrated in FIG. 5B, wherein the acceptable orientations 65*a*, 65*b* are discrete. In response to forces (C), the altered orientation 69 is determined to align with the acceptable discrete orientation 65*b*. Thus, the manipulator controller 52 allows the surgical tool 16 to move from the actual position to the discrete acceptable orientation 65*b*. After movement, the actual orientation of the surgical tool 16 aligns with the acceptable discrete orientation 65*b*.

In instances where there is the preferred subset of the acceptable orientations 65, if the altered orientation 69 corresponds to one of the preferred orientations, the manipulator controller 52 instructs the manipulator 14 to move the surgical tool 16 to the preferred orientation. If the altered orientation 69 does not correspond to one of the preferred orientations but is nonetheless determined to be acceptable, the manipulator controller 52 may instruct the manipulator 14 to move the surgical tool 16 to the non-preferred altered orientation 69. Alternatively, the manipulator controller 52 may instruct the manipulator 14 to move the surgical tool 16 to the preferred orientation nearest to the altered orientation 69.

In some cases, the manipulator controller 52 is configured to allow movement of the surgical tool 16 temporarily to the altered orientation 69 even when determining that the altered orientation 69 does not correspond to the at least one acceptable orientation 65. For example, the manipulator controller 52 may instruct the manipulator 14 to move the surgical tool 16 to the altered orientation 69 only for a predetermined period or distance, or until the surgical tool 16 reaches the next segment in the path 60.

In such scenarios, the manipulator controller 52 is configured to automatically re-orient the surgical tool 16 from the unacceptable altered orientation 69 back to the at least one acceptable orientation 65 after occurrence of a predetermined event. Examples of the predetermined event include, but are not limited to, recognizing a lapse of a predetermined amount of time, traversing a predetermined distance with the surgical tool 16, reaching a subsequent segment of the path, detecting unexpected forces on the surgical tool 16, and the like. The predetermined amount of time, for example, may be based on how long the surgical tool 16 has been in the unacceptable altered orientation 69. Unexpected forces on the surgical tool 16 in the unacceptable altered orientation 69 may occur, for example, from unwanted collisions with an object at the site.

Once the predetermined event is triggered or detected, the orientation regulator instructs the manipulator 14 to re-orient the surgical tool 16 back to the acceptable orientation 65 as the surgical tool 16 continues movement along the path 60. This snap-back feature essentially allows the operator to re-orient the surgical tool 16 temporarily. However, the manipulator controller 52 places the surgical tool 16 immediately back into the at least one acceptable orientation 65 determined by the orientation generator 58. In some instances, the manipulator controller 52 automatically re-orients the surgical tool 16 from the unacceptable altered orientation 69 back to the nearest acceptable orientation 65 after occurrence of the predetermined event. Alternatively, the manipulator controller 52 may automatically re-orient the surgical tool 16 from the unacceptable altered orientation 69 back to one of the preferred orientations.

The surgical tool 16 may also include a manual override button separate from the button used to indicate a desire to alter the orientation. When the manual override button is depressed, the surgical tool 16 may be placed into any altered orientation 69 regardless of whether the altered orientation 69 falls within the at least one acceptable orientation 65. The manual override button may be used when there is an object to be avoided and the robotic control system 24 does not allow the operator to place the surgical tool 16 into any altered orientation 69 that avoids the object. In some cases, when the manual override button is employed, the manipulator controller 52 does not snap the orientation of the surgical tool 16 back into the at least one preferred orientation or other acceptable orientation 65.

If the evaluator 66 determines the altered orientation 69 is within the at least one acceptable orientation 65, the manipulator controller 52 may store the altered orientation 69. As such, if the surgical tool 16 returns to the same relative path segment, or is within a predetermined distance of the same relative path segment, for any reason, the manipulator controller 52 directs the manipulator 14 to re-orient the surgical tool 16 in accordance with the altered orientation 69. Thus, the operator's reorientation of the surgical tool 16 may act to teach the manipulator controller 52 desired orientations while cutting along the path.

Any computer or controller referenced herein, unless otherwise described, includes memory, storage, central processing unit (CPU) with one or more processors or microprocessors, input/output devices, etc. The term "memory" is intended to include non-transitory memory associated with a processor or CPU, such as, for example, RAM (random access memory), ROM (read only memory), a fixed memory device (for example, hard drive), a removable memory device (for example, diskette), a flash memory and the like.

As will be appreciated by one skilled in the art, aspects of the present invention may take the form of a computer program product embodied in one or more computer readable medium(s) having computer readable program code embodied thereon. Computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A robotic system comprising:
a surgical tool being moveable along a path;
a manipulator supporting said surgical tool and being configured to move said surgical tool along the path;
a path generator being configured to determine the path;
an orientation generator being configured to determine at least one acceptable orientation for said surgical tool with respect to the path;
a manipulator controller in communication with said path generator and said orientation generator and being configured to instruct said manipulator to autonomously move said surgical tool in the at least one acceptable orientation along the path as determined;
a sensor being configured to sense forces applied to said surgical tool; and
wherein said manipulator controller is configured to identify an altered orientation based on forces sensed by said sensor and to instruct movement of said surgical tool to the altered orientation along the path in response to comparing the altered orientation to the at least one acceptable orientation.

2. The robotic system of claim 1 wherein said manipulator controller is configured to maintain said surgical tool in the at least one acceptable orientation in response to comparing the altered orientation to the at least one acceptable orientation.

3. The robotic system of claim 2 wherein said manipulator controller is configured to maintain said surgical tool in the at least one acceptable orientation in response to determining that the altered orientation does not correspond to the at least one acceptable orientation.

4. The robotic system of claim 1 wherein said manipulator controller is configured to instruct movement of said surgical tool to the altered orientation in response to determining that altered orientation corresponds to the at least one acceptable orientation.

5. The robotic system of claim 1 wherein said manipulator controller is configured to allow movement of said surgical tool temporarily to the altered orientation in response to determining that the altered orientation does not correspond to the at least one acceptable orientation.

6. The robotic system of claim 5 wherein said manipulator controller is configured to automatically re-orient said surgical tool from the altered orientation back to the at least one acceptable orientation after occurrence of a predetermined event.

7. The robotic system of claim 1 wherein the at least one acceptable orientation includes a plurality of acceptable orientations.

8. The robotic system of claim 7 wherein the plurality of acceptable orientations are defined within a range.

9. The robotic system of claim 7 wherein at least one preferred orientation is defined among the plurality of acceptable orientations.

10. The robotic system of claim 1 wherein the path includes a plurality of path segments and wherein said orientation generator is configured to determine the at least one acceptable orientation with respect to each of the plurality of path segments.

11. A method of controlling a surgical tool of a robotic system during autonomous movement of the surgical tool, said method comprising the steps of:
determining a path of movement for the surgical tool;
determining at least one acceptable orientation of the surgical tool with respect to the path;
autonomously moving the surgical tool along the path in the at least one acceptable orientation;
sensing forces applied to the surgical tool;
identifying an altered orientation based on the sensed forces; and
autonomously moving the surgical tool to the altered orientation along the path in response to comparing the altered orientation to the at least one acceptable orientation.

12. The method of claim 11 wherein autonomously moving the surgical tool along the path in response to comparing the altered orientation to the at least one acceptable orientation includes maintaining the surgical tool in the at least one acceptable orientation.

13. The method of claim 12 wherein maintaining the surgical tool in the at least one acceptable orientation occurs in response to determining that the altered orientation does not correspond to the at least one acceptable orientation.

14. The method of claim 11 wherein autonomously moving the surgical tool to the altered orientation occurs in response to determining that the altered orientation corresponds to the at least one acceptable orientation.

15. The method of claim 11 wherein autonomously moving the surgical tool to the altered orientation occurs temporarily if the altered orientation does not correspond to the at least one acceptable orientation.

16. The method claim 15 further including automatically re-orienting the surgical tool from the altered orientation back to the at least one acceptable orientation after occurrence of a predetermined event.

17. The method of claim 11 wherein determining the at least one acceptable orientation includes determining the at least one acceptable orientation with respect to each of a plurality of path segments defined along the path.

18. The method of claim 11 wherein sensing forces applied to the surgical tool occurs in response to attempting to place the surgical tool in the altered orientation.

19. The method of claim 11 wherein determining the at least one acceptable orientation with respect to the path includes determining the at least one acceptable orientation for allowing the surgical tool to avoid an obstacle along the path.

20. The method of claim 11 wherein determining the at least one acceptable orientation with respect to the path includes determining the at least one acceptable orientation for optimizing cutting efficiency of the surgical tool along the path.

21. A method of controlling a surgical tool of a robotic system during autonomous movement of the surgical tool, said method comprising the steps of:
    determining a path of movement for the surgical tool;
    determining at least one acceptable orientation of the surgical tool with respect to the path;
    autonomously moving the surgical tool along the path in the at least one acceptable orientation;
    sensing forces applied to the surgical tool in response to attempting to place the surgical tool in an altered orientation;
    identifying the altered orientation based on the sensed forces; and
    autonomously moving the surgical tool along the path in response to comparing the altered orientation to the at least one acceptable orientation.

22. The method of claim 21 wherein autonomously moving the surgical tool along the path in response to comparing the altered orientation to the at least one acceptable orientation includes maintaining the surgical tool in the at least one acceptable orientation in response to determining that the altered orientation does not correspond to the at least one acceptable orientation.

23. The method of claim 21 wherein autonomously moving the surgical tool along the path in response to comparing the altered orientation to the at least one acceptable orientation includes moving the surgical tool to the altered orientation in response to determining that the altered orientation corresponds to the at least one acceptable orientation.

24. The method of claim 21 wherein autonomously moving the surgical tool along the path in response to comparing the altered orientation to the at least one acceptable orientation includes moving the surgical tool to the altered orientation temporarily if the altered orientation does not correspond to the at least one acceptable orientation.

25. The method of claim 21 wherein determining the at least one acceptable orientation includes determining the at least one acceptable orientation with respect to each of a plurality of path segments defined along the path.

26. The method of claim 21 wherein determining the at least one acceptable orientation with respect to the path includes one or more of:
    determining the at least one acceptable orientation for allowing the surgical tool to avoid an obstacle along the path; and
    determining the at least one acceptable orientation for optimizing cutting efficiency of the surgical tool along the path.

* * * * *